(12) United States Patent
Kourtakis et al.

(10) Patent No.: US 7,745,672 B2
(45) Date of Patent: Jun. 29, 2010

(54) CATALYTIC CONVERSION OF ETHANOL AND METHANOL TO AN ISOBUTANOL-CONTAINING REACTION PRODUCT USING A THERMALLY DECOMPOSED HYDROTALCITE/METAL

(75) Inventors: Kostantinos Kourtakis, Media, PA (US); Michael B. D'Amore, Wilmington, DE (US); Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/196,602

(22) Filed: Aug. 22, 2008

(65) Prior Publication Data

US 2009/0054703 A1 Feb. 26, 2009

Related U.S. Application Data

(60) Provisional application No. 60/965,726, filed on Aug. 22, 2007.

(51) Int. Cl.
 *C07C 29/34* (2006.01)
 *C07C 29/32* (2006.01)
(52) U.S. Cl. .................. 568/902.2; 568/902; 568/905
(58) Field of Classification Search ................. None
 See application file for complete search history.

(56) References Cited

U.S. PATENT DOCUMENTS 5,095,156 A 3/1992 Radlowski et al.
5,300,695 A 4/1994 Radlowski
5,559,275 A 9/1996 Barger

OTHER PUBLICATIONS

International Search Report and Written Opinion, PCT/US2008/073991, Aug. 22, 2008.
Carlini et al., "Guerbet condensation of methanol with n-propanol to isobutyl alcohol over heterogeneous bifunctional catalysts based on Mg-Al mixed oxides partially substituted by different metal components". Journal of Molecular Catalysis, vol. 232, No. 1-2, pp. 13-20, May 3, 2005.
J. I. Discosimo et al., Structural Requirements and Reaction Pathways in Condensation Reactions of Alcohols on Mg AlO Catalysts, Journal of Catalysis, 2000, vol. 190:261-275.
C. Carlini et al., Guerbet Condensation of Methanol With N-Propanol to Isobutyl Alcohol Over Heterogeneous Bifunctional Catalysts Based on Mg-Al Mixed Oxides Partially Sunstituted by Different Metal Components, Journal of Molecular Catalysis A: Chemical, 2005, vol. 232:13-20.
C. Carlini et al., Guerbet Condensation of Methanol with N-Propanol to Isobutyl Alcohol Over Heterogeneous Copper Chromite/Mg-Al Mixed Oxides Catalysts, Journal of Molecular Catalysis A: Chemical, 2004, vol. 220:215-220.
V. K. Diez et al., Effect of the Acid-Base Properties of Mg-Al Mixed Oxides on the Catalyst Deactivation During Aldol Condensation Reactions, Latin American Applied Research, 2003, vol. 33:79-86.
N. N. Das et al., Catalytic Characterization of Bi-Functional Catalysts Derived From Pd-Mg-Al Layered Double Hydroxides, Bull. Mater. Sci., 2002, vol. 25:283-289.

*Primary Examiner*—Brian J Davis

(57) ABSTRACT

Hydrotalcite/metal carbonate combinations are partially or fully thermally decomposed to provide catalysts useful for the conversion of ethanol and methanol to a reaction product comprising isobutanol.

13 Claims, 2 Drawing Sheets

CATALYTIC CONVERSION OF ETHANOL AND METHANOL TO AN ISOBUTANOL-CONTAINING REACTION PRODUCT USING A THERMALLY DECOMPOSED HYDROTALCITE/METAL

CROSS-REFERENCE TO RELATED APPLICATIONS

This application claims benefit of priority from Provisional Application No. 60/965,726, filed Aug. 22, 2007. This application relates to commonly-assigned applications filed concurrently on Aug. 22, 2008 as Ser. Nos. 12/196,485, 12/196,518, 12/196,540, 12/196,578, and 12/196,651.

FIELD OF THE INVENTION

The present invention relates to the catalytic conversion of ethanol plus methanol to an isobutanol-containing reaction product. Various organic chemicals, including isobutanol itself, can be separated from the reaction product. The catalysts are combinations of hydrotalcites (optionally containing transition metals) and metal carbonates, which combinations have been thermally decomposed, either partially or fully, to form catalytically active species.

BACKGROUND

Efforts directed at improving air quality and increasing energy production from renewable resources have resulted in renewed interest in alternative fuels, such as ethanol and butanol, that might replace gasoline and diesel fuel, or be used as additives in gasoline and diesel fuel.

Methods for producing isobutanol from methanol and other alcohols, particularly ethanol, are known. It is known that isobutanol can be prepared by condensation of ethanol and methanol over basic catalysts at high temperature using the so-called "Guerbet Reaction." See for example, J. Logsdon in Kirk-Othmer Encyclopedia of Chemical Technology, John Wiley and Sons, Inc., New York, 2001.

In addition, U.S. Pat. No. 5,300,695, assigned to Amoco Corp., discloses processes in which an alcohol having X carbon atoms is reacted over an L-type zeolite catalyst to produce a higher molecular weight alcohol. In some embodiments, a first alcohol having X carbon atoms is condensed with a second alcohol having Y carbon atoms to produce an alcohol having X+Y carbons. In one specific embodiment, ethanol and methanol are used to produce isobutanol using a potassium L-type zeolite.

J. I. DiCosimo, et al., in Journal of Catalysis (2000), 190 (2), 261-275, describe the effect of composition and surface properties on alcohol-coupling reactions using $Mg_yAlO_x$ catalysts for alcohol reactions.

Carlini et al. describe a catalytic reaction of methanol with n-propanol to produce isobutyl alcohol. The involved catalyst is a calcined hydrotalcite in combination with copper chromite. See C. Carlini et al, Journal of Molecular Catalysis A: Chemical (2005), 232 (1-2) 13-20. See also C. Carlini, Journal of Molecular Catalysis A: Chemical (2004), 220 (2), 215-220, in which the catalyst is a mixture of a hydrotalcite with palladium, nickel, rhodium or copper, with the mixture being calcined at 500° C.

Hydrotalcites are layered, double hydroxides of the general formula

$(M^{2+}_{1-x}M^{3+}_x(OH)_2)(A^{n-}_{x/n}) \cdot yH_2O$

The $M^{2+}$ ions can be a variety of divalent cations (e.g., Mg, Ni, Pt, Pd, Zn, Co, Fe, Cu) and the $M^{3+}$ ions can be trivalent Al, Fe or Cr. Some hydrotalcites are described by V. K. Diez, C. R. Apesteguia, and J. I. DiCosimo (*Latin American Applied Research*, 33, 79-86 (2003)) and N. N. Das and S. C. Srivastava (*Bull. Mater. Sci.* 25, (4), 283-289 (2002)).

It has been found that partially or fully thermally decomposed combinations of hydrotalcites (particularly those that incorporate transition metals) and metal carbonates can yield catalysts that are effective for the conversion of ethanol plus methanol to a reaction product that comprises (i.e., contains, among other things) isobutanol.

SUMMARY OF THE INVENTION

Certain combinations of hydrotalcites and metal carbonates, as described herein, are partially or fully thermally decomposed to provide catalysts useful for the conversion of ethanol plus methanol to a reaction product comprising isobutanol.

DESCRIPTION

Figure 1:
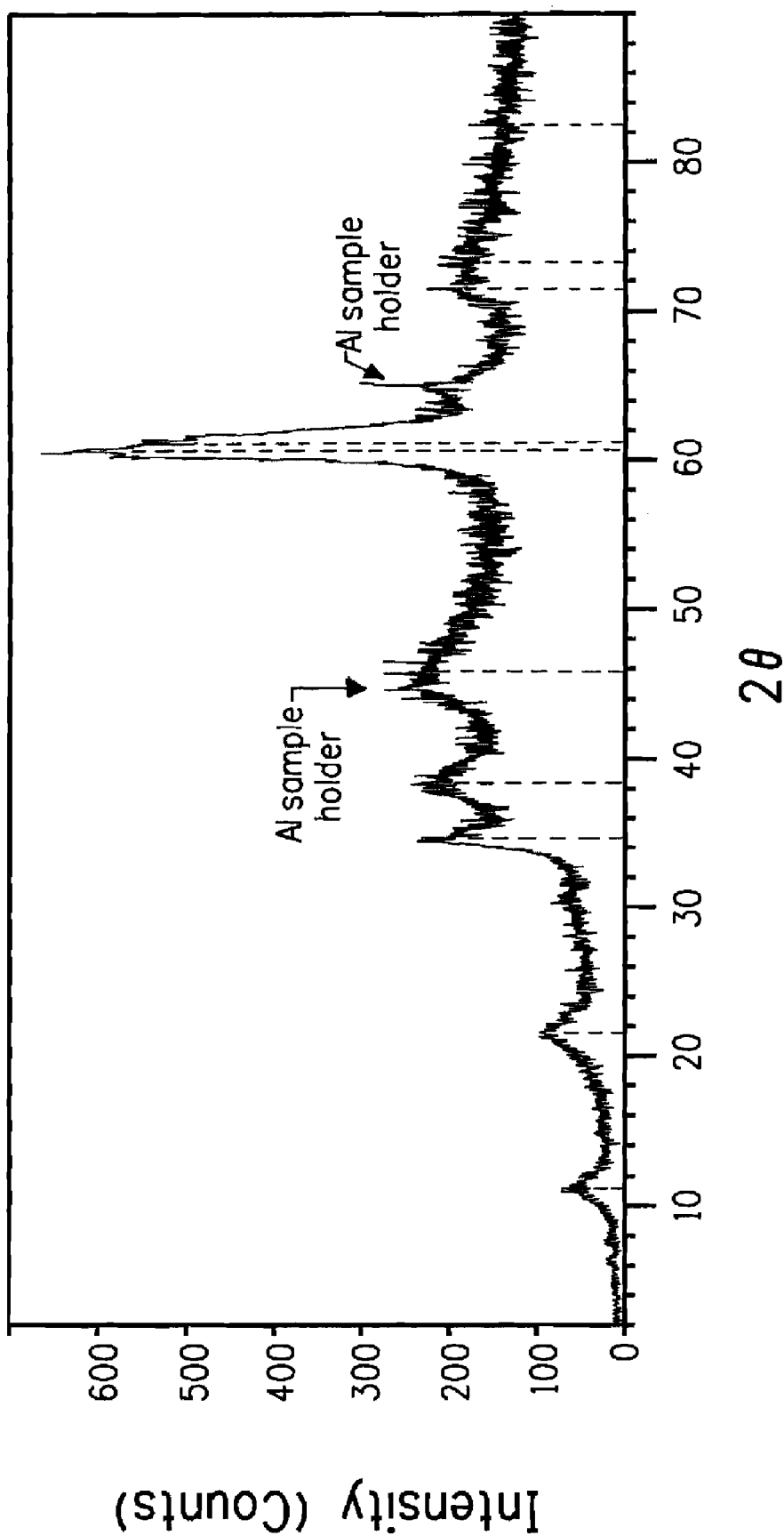
FIG. 1 shows a powder X-ray diffraction pattern of a typical hydrotalcite material before calcination, and indicates reflections typical of a hydrotalcite phase.
Figure 2:
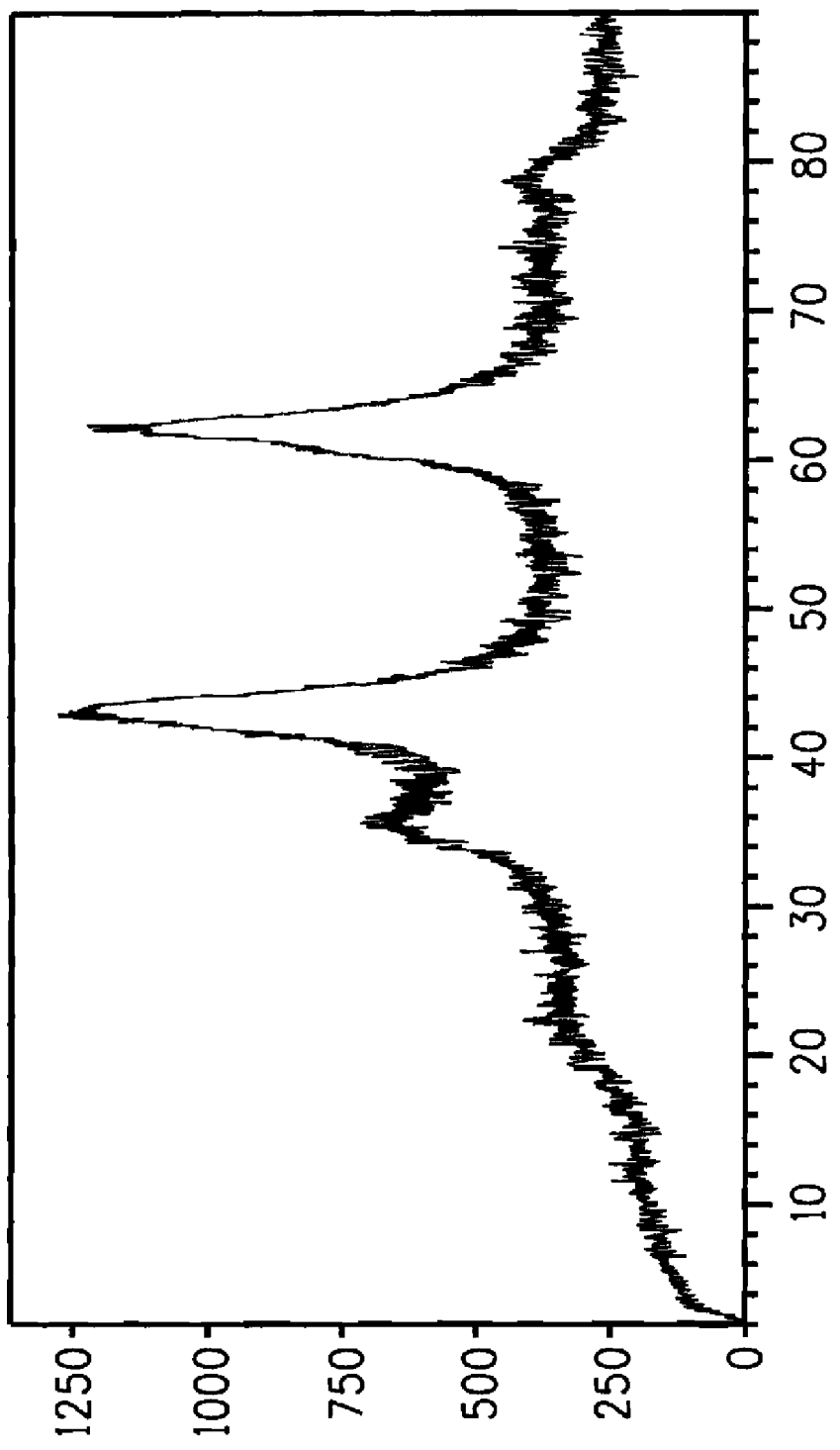
FIG. 2 shows a powder X-ray diffraction pattern of the material of FIG. 1 after calcination, showing decomposition of the hydrotalcite phase by the substantial loss of those reflections that are typical of a hydrotalcite phase.

A vapor stream comprising ethanol and methanol (that may contain some water, and may be diluted with an inert gas such as nitrogen and carbon dioxide) is contacted with at least one thermally decomposed hydrotalcite catalyst at a temperature and pressure sufficient to produce a reaction product comprising water, unreacted ethanol and/or methanol (if less than complete conversion of ethanol and/or methanol), and isobutanol. Butanols other than isobutanol, higher alcohols (higher in the sense that they contain more than 4 carbon atoms) and other organic species may also be produced. Suitable temperatures are in the range of about 150° C. to about 500° C., for example about 200° C. to about 500° C. Suitable pressures are from about 0.1 MPa to about 20.7 MPa. To optimize the production of isobutanol over other organic products, it is preferred that methanol and ethanol are used at a molar ratio of at least about 2 to 1.

The catalysts that are useful in the present invention are partially or fully thermally decomposed hydrotalcite/metal carbonate combinations of a hydrotalcite of the formula $[(M^{2+}_{1-x}M^{3+}_x(OH)_2)(A^{n-}_{x/n}) \cdot yH_2O]$ and a metal carbonate of the formula [M'A']. The combinations, prior to thermal decomposition, have the empirical formula below:

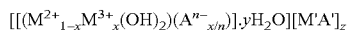

$[[(M^{2+}_{1-x}M^{3+}_x(OH)_2)(A^{n-}_{x/n})] \cdot yH_2O][M'A']_z$ wherein $M^{2+}$ is divalent Mg, or a combination of Mg and at least one divalent member selected from the group consisting of Zn, Ni, Pd, Pt, Co, Fe, and Cu;

$M^{3+}$ is trivalent Al, or a combination of trivalent Al and at least one trivalent member selected from the group consisting of Fe and Cr;

x is 0.66 to 0.1;

$A^{n-}$ is $CO_3^{2-}$ with n=2, or $OH^-$ with n=1;

M'A' is a carbonate of at least one divalent metal M' selected from the group consisting of Zn, Ni, Pd, Pt, Co, Fe, and Cu; and A' is carbonate;

z is any number in the range of 0.001 to 0.5, inclusive (i.e., including the endpoints of the range); and y is 0 to 4.

In a preferred embodiment of this invention, $M^{2+}$ is divalent Mg; $M^{3+}$ is trivalent Al; $A^{n-}$ is $CO_3^{2-}$ or $OH^-$; z is any number between 0.001 and 0.5; and M' is selected from the group consisting of Zn, Ni, Pd, Pt, Co, Fe, and Cu. Preferred values for M' are Ni, Co, and Cu. Preferred values for z are in the range between 0.01 and 0.25, including the endpoints of the range.

The catalysts that are useful in the present invention are derived from a hydrotalcite of the formula as defined above by a process comprising heating the hydrotalcite for a time and at a temperature sufficient to cause a diminution in the hydrotalcite powder X-ray diffraction pattern peak intensities between 2θ angles of 10 degrees and 70 degrees using CuKα radiation.

Catalysts derived from the hydrotalcite can be synthesized by the following method. An aqueous salt solution containing (a) magnesium and one or more divalent metals selected from the group consisting of zinc, nickel, palladium, platinum, cobalt, iron, and copper and (b) aluminum and, optionally, one or more trivalent metals selected from the group consisting of iron and chromium is prepared. Preferred salts are nitrates, chlorides, or acetates. Most preferred are nitrates. The salt solution is added to a basic, aqueous solution containing sodium or potassium carbonate (or bicarbonate), sodium, potassium or ammonium hydroxide, or a mixture of the foregoing carbonates, bicarbonates and hydroxides, thereby providing the carbonate ion or hydroxide ion for $A^{n-}$, as well as the carbonate ion for A'. The pH of this basic solution is typically adjusted to a pH of approximately 10 during the addition of the aqueous salt solution. The (a) magnesium and at least one other divalent metal and the (b) aluminum and optional trivalent metals should be in a molar ratio (a)/(b) between 0.5/1 and 9/1 inclusive (i.e., including the endpoints of the range) to satisfy the stoichiometry of the hydrotalcite component of the above formula. In practice, however, the endpoints of the range should exceed 0.5/1 and 9/1 by an amount sufficient to satisfy the value of "z" for the [M'A'] component of the formula. This is because the metal M' is selected from the same group of metals as the metals that can substitute for divalent magnesium in the hydrotalcite component of the formula. (Alternatively, a plurality of individual metal salt solutions may be used, provided that they are added concurrently to the basic, aqueous solution containing the carbonate, bicarbonate, hydroxide or mixtures thereof.)

The resulting suspension that is formed (i.e., a precipitate suspended in a liquid) can be aged, preferably for approximately 18 hours, at 60° C. to 70° C. The precipitate is then separated, generally by filtering, and subsequently dried (generally in a vacuum oven or in air). The dried precipitate can be analyzed by powder X-ray diffraction to confirm the presence of a hydrotalcite phase. This phase is isostructural with the hydrotalcite $Mg_6Al_2(CO_3)(OH)_{16} \cdot 4H_2O$ (JCPDS card #54-1030; Powder Diffraction Files, International Centre for Diffraction Data, 1601 Park Lane, Swarthmore, Pa. 19081). The dried precipitate is then calcined by heating it for a time and at a temperature sufficient to cause a diminution in the hydrotalcite powder X-ray diffraction pattern peak intensities between 2θ angles of 10 degrees and 70 degrees using CuKα radiation. The calcined material can be analyzed by powder X-ray diffraction to confirm the diminution (including the complete absence) in these peak intensities and the appearance of new peaks corresponding to a material which is isostructural with partially crystalline magnesium oxide (MgO, JCPDS card #65-0476). It is preferred to calcine the dried precipitate for a time and at a temperature sufficient to substantially reduce the peak intensities characteristic of the hydrotalcite phase.

Although any calcination protocol can be used, one that is particularly useful on a laboratory scale includes heating the hydrotalcite in a one inch (2.5 cm) diameter tube furnace from about 25° C. to about 360° C. over 140 minutes at 2.4° C. per minute, and then holding at 360° C. for about 2 to about 4 hours.

The catalysts usable in the process of the invention can be prepared as described above. The catalysts may be used in the form of powders, granules, or other particulate forms. Selection of an optimal average particle size for the catalyst will depend upon such process parameters as reactor residence time and desired reactor flow rates.

The catalytic conversion of ethanol plus methanol to the reaction product comprising isobutanol can be run in either batch or continuous mode as described, for example, in H. Scott Fogler, (*Elements of Chemical Reaction Engineering*, $2^{nd}$ Edition, (1992) Prentice-Hall Inc, CA). Suitable reactors include fixed-bed, adiabatic, fluid-bed, transport bed, and moving bed.

It is preferable, but not essential, to treat the catalyst, prior to its use, with nitrogen or air at elevated temperatures, which is thought to remove unwanted carbonates from the catalyst surface. If the starting hydrotalcite contains nickel, palladium, platinum, cobalt or copper, it is also preferred, but not essential, to treat the catalyst, prior to its use, with hydrogen at elevated temperatures. One protocol that has been found to be effective is described in more detail in Example 1, below. If catalyst treatment is desired, the catalyst may be treated in situ in the reactor or ex situ and then introduced into the reactor.

During the course of the reaction, the catalyst may become fouled, and therefore it may be necessary to regenerate the catalyst. Preferred methods of catalyst regeneration include, contacting the catalyst with a gas such as, but not limited to, air, steam, hydrogen, nitrogen or combinations thereof, at an elevated temperature, although care must be taken not to use a temperature that is so high that the regeneration results in a loss of surface area or other unwanted effects. If catalyst regeneration is desired, the catalyst may be regenerated in situ in the reactor or ex situ and then introduced into the reactor.

One skilled in the art will know that conditions, such as temperature, catalytic metal, catalyst support, reactor configuration and time can affect the reaction kinetics, product yield and product selectivity. Standard experimentation can be used to optimize the yield of isobutanol from the reaction.

Isobutanol can be separated from the reaction product by known chemical engineering methods, including distillation. Other specific chemicals (or combinations of chemicals) also can be removed from the reaction product using known chemical engineering methods. The specific methods will be dependent on the nature of the reaction product, which, in turn, is dependent on the specific catalyst used and the reaction conditions, particularly the extent of conversion of ethanol and methanol.

EXAMPLES

Example 1

$[[(M^{2+}_{1-x}M^{3+}_{x}(OH)_2)(A^{n-}_{x/n})] \cdot yH_2O][M'A']_z$ hydrotalcite $M^{2+}$ is Mg; $M^{3+}$ is Al; x is 0.25; $A^{n-}$ is $CO_3^{2-}$ with n=2; M' is $Ni^{2+}$; A' is $CO_3^{2-}$; z=0.012; and y=0 to 4

8.2 g of sodium bicarbonate (EMD Sciences, Gibbstown N.J.) was dissolved in 250 milliliters (ml) water in a three neck, round bottom flask. The solution was heated to 65° C., and the pH was adjusted to approximately 10 using 2 M sodium hydroxide solution (Mallinckrodt Baker, Phillipsburg, N.J.). 27.5 g of aluminum nitrate $(Al(NO_3)_3 \cdot 9H_2O$ (EMD Sciences, Gibbstown, N.J.)), 57.6 g of magnesium nitrate $(Mg(NO_3)_2 \cdot 6H_2O$ (EMD Sciences)) and 1.07 g of nickel nitrate $(Ni(NO_3)_2 \cdot 6H_2O$ (Sigma-Aldrich, St. Louis, Mo.)) were each dissolved in 100 ml of water and concurrently added drop-wise to the preheated solution containing sodium bicarbonate. After complete addition of the metal nitrate solutions, the suspension was kept at 65° C. with stirring for 1 hr and then aged at this temperature for 18 hours without stirring.

The precipitate was separated from solution by filtering. The precipitate was dried in a vacuum oven at 90° C. for 48 hours and calcined at 360° C. for 2 hours in nitrogen. The heating protocol was as follows: the precipitate was placed in a 1 inch (2.5 cm) diameter tube furnace, and the temperature was raised from 25° C. to 360° C. at 2.4° C./minute over 140 minutes, and held at 360° C. for 2 hours. The catalyst was evaluated according to the procedure described below.

Reactor Evaluation

Approximately 2 cubic centimeters (cc) of catalyst was loaded on a stainless steel mesh support within a 18 inch×½ inch (45.7 cm×1.3 cm) outside diameter (o.d.) type 360 stainless steel tube reactor with inlets for gas and liquid feeds. The catalyst was then pre-conditioned in situ in the reactor by flowing nitrogen gas, initially at room temperature, raising the temperature to 350° C., holding it there for one hour, lowering the temperature to 180° C., flowing hydrogen gas at 15 cc/min for one hour, and reintroducing nitrogen gas at a flow rate of 15 cc/min. The reactor temperature was increased to 300° C., and a mixed stream of methanol and ethanol at a weight ratio of 5 to 1 was introduced. At reaction temperature nitrogen flow was set at 15 cc/min and the flow of the mixed stream of methanol and ethanol was set at 1.03 ml/hr. After 60 minutes, reaction off-gases were condensed over a five minute period into cold N-methylpyrrolidone, and the resultant solution was analyzed using an Agilent™ 5890 GC (Palo Alto, Calif.) equipped with flame ionization and mass selective detectors. Results are shown in Table 1, wherein "EtOH" means ethanol, "i-BuOH" means isobutanol, "Conv." means conversion, and "Sel." means selectivity. Ethanol conversion (%) was calculated as follows: [(1−carbon moles of unreacted ethanol)/carbon moles of total outlet gases] times 100. Selectivity (%) was calculated as follows: (moles of i-BuOH/moles of ethanol reacted) times 100.

TABLE 1

| Temp. ° C. | Minutes | EtOH Conv. | i-BuOH Sel. |
|---|---|---|---|
| 300 | 60 | 76.7 | 7.9 |
| 350 | 60 | 73.5 | 5.9 |
| 400 | 60 | 84.5 | 7.1 |

Example 2

$[[(M^{2+}_{1-x}M^{3+}_{x}(OH)_2)(A^{n-}_{x/n})] \cdot yH_2O][M'A']_z$ hydrotalcite $M^{2+}$ is Mg; $M^{3+}$ is Al; x is 0.25; $A^{n-}$ is $CO_3^{2-}$ with n=2; M' is $Co^{2+}$; A' is $CO_3^{2-}$; z=0.012; and y=0 to 4

8.2 g of sodium bicarbonate (EMD Sciences, Gibbstown N.J.) was dissolved in 250 ml water in a three neck, round bottom flask. The solution was heated to 65° C., and the pH was adjusted to approximately 10 using 2 M sodium hydroxide solution (Mallinckrodt Baker, Phillipsburg, N.J.). 27.5 g of aluminum nitrate $(Al(NO_3)_3 \cdot 9H_2O$ (EMD Sciences, Gibbstown, N.J.)), 57.6 g of magnesium nitrate $(Mg(NO_3)_2 \cdot 6H_2O$ (EMD Sciences)) and 0.92 g of copper nitrate $(Cu(NO_3)_2 \cdot 2.5H_2O$ (Alfa Aesar, Ward Hill, Mass.)) were each dissolved in 100 ml of water and concurrently added drop-wise to the preheated solution containing sodium bicarbonate. After complete addition of the metal nitrate solutions, the suspension was kept at 65° C. with stirring for 1 hour and then aged at this temperature for 18 hours without stirring.

The precipitate was separated from solution by filtering. The precipitate was dried in a vacuum oven at 90° C. for 48 hours and calcined at 360° C. for 2 hours in nitrogen. The heating protocol was as follows: the precipitate was placed in a 1 inch (2.5 cm) diameter tube furnace, and the temperature was raised from 25° C. to 360° C. at 2.4° C./minute over 140 minutes, and held at 360° C. for 2 hours. The catalyst was evaluated according to the procedure described in Example 1. Results are shown in Table 2.

TABLE 2

| Temp. ° C. | Minutes | EtOH Conv. | i-BuOH Sel. |
|---|---|---|---|
| 300 | 60 | 38.6 | 2.4 |
| 350 | 60 | 80.0 | 6.0 |
| 400 | 60 | 77.4 | 6.4 |

What is claimed is:

1. A process for making a isobutanol-containing reaction product, comprising:
   contacting a reactant comprising ethanol and methanol with a catalyst at a reaction temperature and pressure sufficient to produce said reaction product, wherein said catalyst is derived from a hydrotalcite of the formula:

$[[(M^{2+}_{1-x}M^{3+}_{x}(OH)_2)(A^{n-}_{x/n})] \cdot yH_2O][M'A']_z$ wherein,
   $M^{2+}$ is divalent Mg, or a combination of Mg and at least one divalent member selected from the group consisting of Zn, Ni, Pd, Pt, Go, Fe, and Cu;
   $M^{3+}$ is trivalent Al, or a combination of trivalent Al and at least one trivalent member selected from the group consisting of Fe and Cr;
   x is 0.66 to 0.1;
   $A^{n-}$ is $CO_3^{2-}$ with n=2, or $OH^-$ with n=1;

M'A' is a carbonate of at least one divalent metal M' selected from the group consisting of Zn, Ni, Pd, Pt, Go, Fe, and Cu; and A' is carbonate;

z is any number between 0.001 and 0.5 inclusive; and y is 0 to 4, wherein the hydrotalcite catalyst is partially decomposed.

2. The process of claim 1, wherein the decomposition is achieved by heating for a time and at a temperature sufficient to cause a diminution in the hydrotalcite powder X-ray diffraction pattern peak intensities between 2θ angles of 10 degrees and 70 degrees using CuKα radiation.

3. The process of claim 1, wherein $M_{2+}$ is divalent Mg.

4. The process of claim 1, wherein $M_{3+}$ is trivalent Al.

5. The process of claim 1, wherein M' is $Co^{2+}$.

6. The process of claim 1, wherein M' is $Ni^{2+}$.

7. The process of claim 1, wherein $A^{n-}$ is $CO_3^{2-}$.

8. The process of claim 1, wherein x is 0.25.

9. The process of claim 1, wherein n is 2.

10. The process of claim 1, wherein z is 0.012.

11. The process of claim 1, wherein, $M^{2+}$ is $Mg^{2+}$; $M^{3+}$ is $Al^{3+}$; x is 0.25; $A^{n-}$ is $CO_3^{2-}$; n is 2; M' is $Co^{2+}$; A' is $CO_3^{2-}$; z is 0.012; and y is 0 to 4.

12. The process of claim 1, wherein $M^{2+}$ is Mg; $M^{3+}$ is $Al^{3+}$; x is 0.25; $A^{n-}$ is $CO_3^{2-}$; n is 2; M' is $Ni^{2+}$; A' is $CO_3^{2-}$; z is 0.012; and y is 0 to 4.

13. The process of claim 1, wherein said reaction temperature is from about 200° C. to about 500° C., and said pressure is from about 0.1 MPa to about 20.7 MPa.

* * * * *